United States Patent [19]

Miyake et al.

[11] 4,162,268

[45] Jul. 24, 1979

[54] PROCESS FOR PREPARING DIACETYLBENZENE

[75] Inventors: Tetsuya Miyake; Kohji Noguchi; Kohichi Fujimoto, all of Kawasaki, Japan

[73] Assignee: Asahi Kasei Kogyo K.K., Osaka, Japan

[21] Appl. No.: 840,073

[22] Filed: Oct. 6, 1977

[30] Foreign Application Priority Data

Oct. 22, 1976 [JP] Japan .................................. 51-126188

[51] Int. Cl.$^2$ ............................................. C07C 45/04
[52] U.S. Cl. ............................................................ 260/592
[58] Field of Search ............................................ 260/592

[56] References Cited

U.S. PATENT DOCUMENTS

| 3,714,263 | 1/1973 | Cyba | 260/592 |
| 3,876,688 | 4/1975 | de Raditzky et al. | 260/592 |

FOREIGN PATENT DOCUMENTS 1035856  7/1966  United Kingdom ...................... 260/592

OTHER PUBLICATIONS

Hanotier et al., J.C.S. Perken II, 1973, pp. 381-386.

Sanders, Industrial & Engineering Chemistry, vol. 45, pp. 2-14, (1953).

*Primary Examiner*—James H. Reamer
*Attorney, Agent, or Firm*—Sprung, Felfe, Horn, Lynch & Kramer

[57] ABSTRACT

A process for preparing diacetylbenzene by a liquid phase oxidation reaction which comprises contacting a heterogeneous mixture of (A) about 98 to about 25 percent by volume of an organic liquid phase containing at least one compound selected from the group consisting of diethylbenzene and ethylacetophenone and (B) about 2 to about 75 percent by volume of an aqueous liquid phase containing, as a catalyst, at least about 0.01 mol/l of at least one water-soluble salt of a metal selected from the group consisting of manganese, cobalt, nickel, chromium, copper and iron and having a pH of about 1 to about 6 with a molecular oxygen-containing gas at a temperature of from about 100° C. to about 180° C. under a pressure of about 1 to about 50 Kg/cm$^2$ to effect the liquid phase oxidation reaction, separating the resulting reaction mixture liquid into the aqueous liquid phase and the organic liquid phase and recovering diacetylbenzene from the separated organic liquid phase by distillation.

17 Claims, No Drawings

PROCESS FOR PREPARING DIACETYLBENZENE

BACKGROUND OF THE INVENTION

1. Field of the Invention

This invention relates to a process for preparing diacetylbenzene from diethylbenzene, ethylacetophenone or a mixture thereof by a liquid phase oxidation reaction using a molecular oxygen-containing gas.

2. Description of the Prior Art

Diacetylbenzene is used as an intermediate, for example, for preparing divinylbenzene which is a cross-linking agent for high molecular weight polymers, by a hydrogenation and a dehydration, and for preparing an aromatic diamine by an oximation and a Beckman rearrangement. Also, diacetylbenzene is a starting material for preparing heat resistant polymers and one of the promising compounds for the chemical industry.

In general, in the liquid phase oxidation of an ethyl group bonded to a benzene nucleus, the corresponding carboxylic acid is easily produced. Accordingly, in order to selectively produce an acetyl substituted benzene, which is an intermediate compound in oxidizing the ethyl substituted benzene to the corresponding carboxylic acid, not only are there restrictions on the starting materials, but also it is necessary to take special measures for selecting catalysts and reaction conditions.

Furthermore, in the production of diacetylbenzene which is a difunctional compound the following further restrictions on the reaction conditions and purification methods in addition to those mentioned above are imposed.

A first restriction originates from the reactivity of ethylacetophenone. In general, in the autoxidation reaction of an alkylbenzene the reactivity is in accordance with the Hammett rule and its reaction constant $\rho$ is a negative value. Thus, it is more difficult to oxidize the ethyl group of ethylacetophenone whose acetyl group exhibits a strong electron attraction, and the reaction conditions become more rigorous. As a result, the selectivity to diacetylbenzene tends to decrease, and more severe restrictions on the selection of catalysts and reaction conditions are imposed.

A second restriction arises from the need to suppress the formation of compounds which hinder the oxidation reaction. Namely, in the liquid phase oxidation reaction, compounds which hinder the oxidation reaction are formed as the oxidation reaction proceeds, and the oxidation reaction tends to stop. For this reason the oxidation reaction is carried out at a low conversion in most cases. Thus, when diacetylbenzene is prepared from diethylbenzene at a low conversion, the yield per volume of the reactor is reduced and the quantity of heat for separating the products from the starting material is remarkably increased. Furthermore, since the oxidation reaction of diethylbenzene to diacetylbenzene is a sequential reaction through ethylacetophenone as an intermediate, at low conversions, the oxidation reaction stops at the ethylacetophenone stage, and as a result very little diacetylbenzene is formed. Thus, in this oxidation reaction the formation of compounds which hinder the oxidation reaction must be suppressed to achieve a high conversion.

A third restriction arises in the purification of diacetylbenzene. Since diacetylbenzene is a difunctional compound having a high boiling point, the decomposition and polymerization of diacetylbenzene take place when diacetylbenzene is distilled in the presence of the catalyst, and therefore the catalyst must be removed prior to the distillation of the diacetylbenzene.

A fourth restriction is due to the selectivity to diacetylbenzene. Since diacetylbenzene is difunctional compounds, various by-products can be formed, and some of them have a boiling point very close to each other. Thus, since it becomes more difficult to obtain a product of high purity, the selectivity to the products must be high.

Accordingly, in preparing diacetylbenzene from diethylbenzene as a starting material on an industrial scale, the purification system must be taken into account in addition to the oxidation reaction system. More specifically, a technique must be established in which the oxidation reaction at a high conversion of the starting material can be achieved while the formation of compounds hindering the oxidation reaction is suppressed, the selectivity to the product at a high conversion of the starting material is increased, and a regenerable catalyst can be efficiently separated from the reaction mixture liquid.

It is known that diacetylbenzene can be prepared by the liquid phase oxidation of diethylbenzene as a starting material using an oil-soluble metal salt catalyst such as a naphthenate of a transition metal. However, according to this method the decomposition of diacetylbenzene partially takes place in the separation procedure using a distillation after the oxidation reaction and it is difficult to obtain the product in high purity with high yield. On the other hand, Japanese Patent Application (OPI) 72231/1974 describes a method of purifying diacetylbenzene which comprises treating the reaction mixture, which has been obtained by the liquid phase oxidation of diethylbenzene using oxygen or an oxygen-containing gas and which contains, as the main component, diacetylbenzene, as such or after a flash distillation, with an alkali and distilling the reaction mixture thus treated. When the catalyst is removed according to this invention, it is necessary to provide another step of regenerating the recovered catalyst for reuse.

SUMMARY OF THE INVENTION

According to the present invention there is provided a process for preparing diacetylbenzene by the liquid phase oxidation reaction which comprises contacting a heterogeneous mixture of (A) about 98 to about 25 percent by volume of an organic liquid phase containing at least one compound selected from the group consisting of diethylbenzene and ethylacetophenone and (B) about 2 to about 75 percent by volume of an aqueous liquid phase containing, as a catalyst, at least about 0.01 mol/l of at least one water-soluble salt of a metal selected from the group consisting of manganese, cobalt, nickel, chromium, copper and iron and having a pH of about 1 to about 6 with a molecular oxygen-containing gas at a temperature of about 100° C. to about 180° C. under a pressure of about 1 to about 50 Kg/cm² to effect the liquid phase oxidation reaction, separating the resulting reaction mixture liquid into the aqueous liquid phase and the organic liquid phase and recovering diacetylbenzene from the separated organic liquid phase by distillation.

DETAILED DESCRIPTION OF THE INVENTION

Suitable starting materials which may be employed in this invention include the para-, meta- and ortho-isomers of diethylbenzene and ethylacetophenone and any mixtures thereof. In general, a mixture of para-isomer and meta-isomer of diethylbenzene in a weight ratio of about 30 to about 70 which is by-produced in the preparation of ethylbenzene can be advantageously employed. Also p-ethylacetophenone which is obtained in the acetylation of ethylbenzene and is easily available can be quite suitably used as a starting material, and p-diacetylbenzene can be prepared therefrom.

In preparing diacetylbenzene from diethylbenzene according to this invention, first, one of the two ethyl groups of the diethylbenzene is oxidized to form ethylacetophenone and, second, the ethyl group of the resulting ethylacetophenone is oxidized to form diacetylbenzene. Thus, two oxidation steps are involved in the preparation of diacetylbenzene from diethylbenzene and accordingly two processes are possible. One process is a two-step method comprising isolating, as an intermediate, the ethylacetophenone obtained in the first oxidation step and converting the ethylacetophenone into diacetylbenzene in the second oxidation step. The other process is a one-step method comprising conducting the two oxidation steps sequentially without isolating the ethylacetophenone as an intermediate. According to the two-step method, the isolated ethylacetophenone contains α-ethylphenylethanol which is the corresponding alcohol derivative but this compound can be ultimately converted into diacetylbenzene. In general, the two-step method requires the use of more complicated equipment for preparing diacetylbenzene than the one step method.

Appropriate catalysts which can be employed in this invention are water-soluble salts of manganese, cobalt, nickel, chromium, copper and iron. Of these water-soluble metal salts, manganese salts and cobalt salts are preferred. Suitable water-soluble salts which can be used include organic acid salts and inorganic acid salts. Examples of organic acid salts include, for example, the acetates and propionates, and examples of inorganic acid salts include, for example, the sulfates, nitrates and chlorides. Of these salts, the acetates are preferred. With regard to the oxidation state of the metal in the salts, manganese (II), cobalt (II), nickel (II), chromium (III), copper (II) and iron (III) are preferred.

Specific examples of suitable catalysts include manganese (II) acetate, manganese (II) propionate, manganese (II) sulfate, manganese (II) nitrate, manganese (II) chloride, cobalt (II) acetate, cobalt (II) propionate, cobalt (II) sulfate, cobalt (II) nitrate, cobalt (II) chloride, nickel (II) acetate, nickel (II) propionate, nickel (II) sulfate, nickel (II) nitrate, nickel (II) chloride, chromium (III) acetate, chromium (III) propionate, chromium (III) sulfate, chromium (III) nitrate, chromium (III) chloride, iron (III) acetate, iron (III) propionate, iron (III) sulfate, iron (III) nitrate and iron (III) chloride and any mixtures thereof.

The catalysts used in the process of this invention are employed in the form of an aqueous solution thereof.

A suitable concentration of the catalyst in the aqueous liquid phase which is required in the process of the present invention is at least about 0.01 mol/l. When the concentration of the catalyst is less than about 0.01 mol/l the rate of the oxidation reaction is reduced and the selectivity to diacetylbenzene is decreased. A preferred concentration of the catalyst is 0.05 mol/l or more, and a more preferred concentration of the catalyst ranges from 0.1 to 1.0 mol/l.

The presence of an aqueous liquid phase in the oxidation reaction is essential in the process of this invention. The presence of the aqueous liquid phase not only facilitates separation of the catalyst in the recovery process for the catalyst after the oxidation reaction but also suppresses the production of by-products to provide a high selectivity to the products at a high conversion. Thus, the amount of the aqueous liquid phase, based on the total volume of the liquid, which is necessary in this invention is at least about 2 percent by volume. When the amount of the aqueous liquid phase is less than about 2 percent by volume, a stable emulsion tends to form and the separation and recovery of the catalyst after the oxidation reaction become difficult. Also, from the viewpoint of productivity, the amount of the aqueous liquid phase is at most about 75 percent by volume. A preferred amount of the aqueous liquid phase ranges from 5 to 60 percent by volume and a more preferred amount ranges from 10 to 50 percent by volume.

The pH of the aqueous liquid phase is adjusted with an acid whose anion corresponds to the anion of the catalyst alone or with sulfuric acid or an aqueous solution of ammonia to prevent the formation of precipitates due to the decomposition of the catalyst. The pH of the aqueous liquid phase used in the process of this invention ranges from about 1 to about 6. When the pH of the aqueous liquid phase is lower than about 1, the rate of the oxidation reaction is increased but the selectivity to diacetylbenzene is reduced. On the other hand, when the pH of the aqueous liquid phase is higher than about 6, precipitates are formed by the hydrolysis of the catalyst. A preferred pH of the aqueous liquid phase ranges from 3 to 5.

The molecular oxygen-containing gas which is employed as an oxidizing agent in the process of this invention may be pure oxygen or oxygen diluted with an inert gas such as nitrogen and/or carbon dioxide. Air is preferably employed as the molecular oxygen-containing gas. The oxidation reaction according to the process of this invention proceeds smoothly with at least about one percent by volume of molecular oxygen based on the total gas volume in a reactor. However, the amount of the molecular oxygen present in the gas in the reactor is preferably at most about 15 percent by volume from the viewpoint of avoiding the explosions. A more preferred amount of molecular oxygen ranges from 2 to 10 percent by volume.

The oxidation reaction according to the process of this invention is carried out at a temperature ranging from about 100° C. to about 180° C. In general, when the oxidation reaction temperature is lower than about 100° C., the rate of the oxidation reaction is low, and on the other hand, when the temperature is higher than about 180° C., the selectivity to the product is reduced. The preferred temperature depends upon factors such as the catalyst selected, the concentration of catalyst chosen, the pH of the aqueous liquid phase employed and other factors. When cobalt (II) acetate or manganese (II) acetate is employed in a concentration of 0.2 mol/l and the aqueous liquid phase containing the cobalt (II) acetate or manganese (II) acetate has a pH of 3 to 5, a preferred oxidation reaction temperature with regard to cobalt (II) acetate ranges from 120° C. to 150° C. and with regard to manganese acetate (II) ranges from 130° C. to 160° C.

The effect of the oxidation reaction pressure on the oxidation reaction according to the process of this invention is smaller than that of the oxidation reaction temperature. In general, the rate of the oxidation reaction increases with higher pressures. The present invention requires a pressure sufficient to prevent the reaction mixture solution from volatilizing, and from the viewpoint of apparatus restrictions a lower pressure is preferred. A suitable oxidation reaction pressure according to the process of this invention ranges from about 1 to about 50 Kg/cm$^2$. A preferred pressure ranges from 2 to 30 Kg/cm$^2$ and a more preferred pressure ranges from 3 to 20 Kg/cm$^2$.

In the present invention in order to promote the contact of the starting material with the molecular oxygen-containing gas fine bubbles are preferably maintained in the reaction mixture liquid with sufficient stirring. The oxidation reaction according to the process of this invention will proceed smoothly by maintaining the amount of bubbles in the reaction mixture liquid in a range of typically from about 3 to about 30 percent by volume, and preferably from 5 to 20 percent by volume.

The material of the reactor affects the oxidation reaction of the process of this invention, and a reactor which is corrosion-resistant to the reaction mixture liquid is preferred. For example, when a reactor of iron is employed, the rate of the oxidation reaction is low and the oxidation reaction stops at a low conversion, and, furthermore, the selectivity to diacetylbenzene is remarkably reduced. Preferred materials for the reactor are titanium and glass or reactors lined with titanium or glass. Reactors in which the areas contacting the reaction mixture liquid are lined with titanium or glass are also preferred.

The process according to this invention can be carried out either batchwise, semi-continuously or continuously. In the batchwise process, a mixture of the organic liquid phase containing either diethylbenzene or ethylacetophenone or both of these materials and the aqueous liquid phase containing a specific catalyst as described above is charged in a reactor, and a molecular oxygen-containing gas is fed therein at a specific temperature as described above under a specific pressure as described above with vigorous stirring. In the continuous process the starting material is fed at a constant rate as the oxidation reaction progresses, while the content of the reactor is withdrawn at a constant rate.

In the batchwise process, the concentration of the starting material i.e., the diethylbenzene and/or the ethylacetophenone, in the organic liquid phase fed in a reactor is typically about 100 percent by weight, and when the concentration of diacetylbenzene reaches a level of about 5 to about 70 percent by weight, and preferably a level of about 10 to about 50 percent by weight, the reaction mixture liquid is withdrawn from the reactor. In the continuous process, the concentration of the diethylbenzene and/or the ethylacetophenone as the starting material in the organic liquid phase in a reactor is at least about 10 percent by weight from the viewpoint of the rate of the oxidation reaction. Also, when the concentration of the diacetylbenzene produced is less than about 5 percent by weight, the quantity of heat necessary for recovering the diacetylbenzene produced from the organic liquid phase becomes too large. Thus, the concentration of the diethylbenzene and/or ethylacetophenone in the organic liquid phase in a reactor typically ranges from about 10 to about 95 percent by weight, and preferably ranges from 30 to 90 percent by weight.

The reaction mixture liquid collected is separated into the organic liquid phase and the aqueous liquid phase. The separation of the organic liquid phase from the aqueous liquid phase can be effected using conventional methods such as using a coalescer, settling, centrifuging. The removal of the catalyst is essentially completed in this separation of the organic liquid phase from the aqueous liquid phase, and then the product is recovered from the organic liquid phase by distillation. Where distillation is used as a product recovery method, the decomposition and polymerization of diacetylbenzene and ethylacetophenone, which are observed in the case of an oil-soluble catalyst, are not observed.

According to the process of this invention the selectivity to the product is increased and, as a result, the formation of by-products having a high boiling point due to side reactions is reduced. More specifically, in the distillation of the organic liquid phase separated from the aqueous liquid phase the distillation residue based on the total weight of the diethylbenzene, the ethylacetophenone and the diacetylbenzene fed is at most about 3 percent by weight. Thus, the amount of diacetylbenzene which is lost together with the distillation residue is low, and the recovery rate of diacetylbenzene by distillation based on the weight of the diacetylbenzene fed approaches about 95 to about 98 percent by weight. These high values show that hardly any decomposition and polymerization of diacetylbenzene occur in the distillation.

Furthermore, if necessary or if desired, the organic liquid phase separated from the aqueous liquid phase after the oxidation reaction is treated with either an aqueous acidic solution or an aqueous alkaline solution, either alone or successively with both of these solutions, to remove a minute amount of the catalyst and the by-produced carboxylic acids remaining in the organic liquid phase, and subsequently in recovering the diacetylbenzene by distillation the resulting organic liquid phase is distilled with a higher distillation efficiency. Suitable aqueous acidic solutions which can be used include, for example, dilute aqueous solutions of hydrochloric acid and/or sulfuric acid. Suitable aqueous alkaline solutions which can be used include, for example, dilute aqueous solutions of sodium hydroxide and/or potassium hydroxide.

The distillation of the organic liquid phase in recovering the diacetylbenzene according to the process of this invention may be conducted either at atmospheric pressure or under reduced pressure such as at about 760 mmHg to about 1 mmHg. The boiling points of diethylbenzene, ethylacetophenone and diacetylbenzene are 180° C. to 184° C./760 mmHg, 120° C. to 126° C./20 mmHg and 153° C. to 155° C./10 mmHg, respectively.

The diethylbenzene and ethylacetophenone recovered by distillation can be reused in the oxidation reaction step of the process of this invention as a starting material without any decrease in the rate of the oxidation reaction and the selectivity to the products. Also the aqueous liquid phase separated from the organic liquid phase, if the catalyst concentration is sufficiently high, can be reused without any decrease in the rate of the oxidation reaction and the selectivity to the products, compared with a newly prepared aqueous catalyst solution. However, in the oxidation reaction step of the process of this invention two moles of water based on one mole of diacetylbenzene are formed, and as a result, the concentration of the catalyst in the aqueous liquid phase is reduced. Thus, in continuously carrying out the oxidation reaction step in the process of this invention, the water formed during the oxidation reaction must be removed to maintain the concentration of the catalyst constant. Accordingly in the process of this invention, the aqueous liquid phase separated from the organic liquid phase can be reused for the oxidation reaction step after the concentration of the catalyst in the aqueous liquid phase and the pH of the aqueous liquid phase have been adjusted.

The oxidation reaction step can be monitored using gas chromatographic analysis of the organic liquid phase after the oxidation reaction step. The concentration of the oxygen in the discharged gas can be continuously measured by passing the discharged gas through a meter for measuring the oxygen concentration, and from this result the partial pressure of the oxygen during the oxidation reaction can be calculated. Also from the results of gas chromatography the first order reaction rate constants, $k'_1$ and $k'_2$, the selectivities to the products $S_M$, $S_D$, $S_1$ and $S_2$ and the conversion of the starting material can be obtained as shown below.

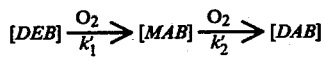

$$\frac{d[DEB]}{dt} = -k'_1[DEB]$$

$$\frac{d[MAB]}{dt} = -k'_2[MAB]$$

$$S_M (\%) = \frac{[MAB]}{[DEB]_o - [DEB]} \times 100$$

$$S_D (\%) = \frac{[DAB]}{[DEB]_o - [DEB]} \times 100$$

($S_M$ and $S_D$ are selectivity indices in the batchwise process.)

$$S_1 (\%) = S_M + S_D$$

$$S_2 (\%) = \frac{[DAB]}{[DEB]_o - [DEB] + [MAB]_o - [MAB]} \times 100$$

($S_1$ and $S_2$ are selectivity indices in the continuous process.)

$$\text{Conversion} (\%) = \frac{[DEB]_o - [DEB]}{[DEB]_o} \times 100$$

wherein [DEB], [MAB] and [DAB], each represents the molar concentration of diethylbenzene, ethylacetophenone and diacetylbenzene in the organic liquid phase after the oxidation reaction, respectively and $[DEB]_o$ represents the molar concentration of diethylbenzene in the starting organic liquid phase.

According to the process of this invention, diacetylbenzene can be prepared with a high selectivity at a high conversion of the starting material by particularly employing a specific catalyst, a specific concentration range for the catalyst in an aqueous phase, a specific pH range for the aqueous liquid phase, a specific oxidation reaction temperature range and pressure range as described above. Also, the separation of the catalyst used in the oxidation reaction can be easily and effectively carried out by employing, as a reaction system, a heterogeneous system of the organic liquid phase containing the starting material and the aqueous liquid phase containing the catalyst.

The present invention will now be illustrated in greater detail by the following Examples.

EXAMPLE 1

In a 500 ml titanium reactor equipped with two baffle plates, a stirrer, a gas inlet nozzle, a sampling nozzle, a reflux condenser, a thermometer, a pressure gauge, a gas flow meter and a meter for measuring oxygen concentration were charged 240 g of diethylbenzene (para-isomer:meta-isomer weight ratio=30:70) and 60 g of a 0.2 mol/l aqueous solution of each of the various catalysts as set forth in Table I below whose pH had been adjusted to 4 with an acid whose anion corresponded to the anion of the catalyst alone or with sulfuric acid and an aqueous solution of ammonia.

After the air in the reactor was replaced by nitrogen gas, the temperature was increased to the temperature as set forth in Table I, and the pressure in the reactor was adjusted to 15 Kg/cm² with stirring at a rate of 1,200 r.p.m. The oxidation reaction was carried out by continuously feeding air as the molecular oxygen-containing gas into the reactor while maintaining the concentration of oxygen in the discharged gas at a level of 3 to 5 percent by volume and controlling the oxidation reaction temperature within ±2° C. of the temperature as set forth in Table I.

During the reaction, the reaction mixture liquid was sampled at intervals and each of the samples was separated into the organic liquid phase and the aqueous liquid phase, and the organic liquid phase separated was gas chromatographed. The results obtained are shown in Table I. The values of the conversion, $S_M$, $S_D$ and $S_1$ are those when the amount of diethylbenzene became nearly constant.

Table I

| Run No. | Catalyst | Reaction Temperature (°C.) | $k'_1$ (sec$^{-1}$) | Conversion (%) | $S_M$ (%) | $S_D$ (%) | $S_1$ (%) |
|---|---|---|---|---|---|---|---|
| 1 | Manganese (II) acetate | 140 | 2.1 × 10$^{-4}$ | 87 | 52 | 25 | 77 |
| 2 | Cobalt (II) acetate | 140 | 4.7 × 10$^{-4}$ | 96 | 51 | 31 | 82 |
| 3 | Copper (II) acetate | 140 | 1.5 × 10$^{-4}$ | 42 | 74 | 12 | 86 |
| 4 | Chromium (III) acetate | 140 | 1.1 × 10$^{-4}$ | 58 | 60 | 16 | 76 |
| 5 | Nickel (II) acetate | 140 | 0.65 × 10$^{-4}$ | 55 | 56 | 10 | 66 |
| 6 | Iron (III) acetate | 140 | 0.65 × 10$^{-4}$ | 46 | 42 | 8 | 50 |
| 7 | Manganese (II) sulfate | 160 | 1.8 × 10$^{-4}$ | 70 | 53 | 18 | 71 |
| 8 | Manganese (II) chloride | 160 | 0.93 × 10$^{-4}$ | 56 | 30 | 8 | 38 |
| 9 | Manganese (II) nitrate | 140 | 1.5 × 10$^{-4}$ | 75 | 47 | 21 | 68 |
| 10 | Manganese (II) propionate | 140 | 1.9 × 10$^{-4}$ | 81 | 50 | 20 | 70 |

EXAMPLE 2

Using the same type of reactor as described in Example 1 the same procedures as described in Example 1 were repeated except that the concentration of the catalyst in the aqueous liquid phase was varied as set forth in Table II below and the concentration of the oxygen in the discharged gas was adjusted to a level of 2 to 10 percent by volume.

The results obtained are shown in Table II. The values of the conversion, $S_M$, $S_D$ and $S_1$ are those when the amount of diethylbenzene became nearly constant.

Table II

| Run No. | Catalyst | Concentration of Catalyst (mol/l) | $k'_1$ (sec$^1$) | Conversion (%) | $S_M$ (%) | $S_D$ (%) | $S_1$ (%) |
|---|---|---|---|---|---|---|---|
| 1 | Manganese (II) acetate | 0.01 | $0.1 \times 10^{-4}$ | 50 | 35 | 4 | 39 |
| 2 | " | 0.04 | $3.9 \times 10^{-4}$ | 84 | 48 | 19 | 67 |
| 3 | " | 0.2 | $6.7 \times 10^{-4}$ | 94 | 51 | 35 | 86 |
| 4 | " | 0.4 | $8.5 \times 10^{-4}$ | 92 | 37 | 33 | 70 |
| 5 | " | 0.8 | $6.6 \times 10^{-4}$ | 90 | 28 | 34 | 62 |
| 6 | " | 1.6 | $6.7 \times 10^{-4}$ | 87 | 38 | 28 | 66 |
| 7 | Cobalt (II) acetate | 0.01 | $0.05 \times 10^{-4}$ | 45 | 31 | 11 | 42 |
| 8 | " | 0.04 | $0.44 \times 10^{-4}$ | 83 | 36 | 15 | 51 |
| 9 | " | 0.2 | $3.1 \times 10^{-4}$ | 91 | 47 | 38 | 85 |
| 10 | " | 0.8 | $3.2 \times 10^{-4}$ | 91 | 47 | 45 | 92 |
| 11 | " | 1.5 | $3.5 \times 10^{-4}$ | 94 | 45 | 42 | 87 |

Reaction temperature:
Manganese (II) acetate: 160° C.
Cobalt (II) acetate: 130° C.

EXAMPLE 3

Using the same type of reactor as described in Example 1 the same procedures as described in Example 1 were repeated except that the pH of the aqueous liquid phase was varied as set forth in Table III below. The pH was adjusted with acetic acid if such were possible to obtain the pH shown, otherwise sulfuric acid or an aqueous solution of ammonia was used.

The results obtained are shown in Table III. The values of the conversion, $S_M$, $S_D$ and $S_1$ are those when the amount of diethylbenzene became nearly constant.

EXAMPLE 4

Using the same type of reactor as described in Example 1 the same procedures as described in Example 1 were repeated except that the oxidation reaction temperature was varied as set forth in Table IV.

The results obtained are shown in Table IV. The values of the conversion, $S_M$, $S_D$ and $S_1$ are those when the amount of diethylbenzene became nearly constant. From these values in Table IV, the activation energy of the oxidation reaction was calculated and the results are as follows:

Cobalt (II) acetate:14.8 Kcal/M
Manganese (II) acetate:20.2 Kcal/M

Table III

| Run No. | Catalyst | pH of Aqueous Phase | $k'_1$ (sec$^1$) | Conversion (%) | $S_M$ (%) | $S_D$ (%) | $S_1$ (%) |
|---|---|---|---|---|---|---|---|
| 1 | Cobalt (II) acetate | 1.0 | $8.0 \times 10^{-4}$ | 80 | 27 | 25 | 52 |
| 2 | " | 3.0 | $2.7 \times 10^{-4}$ | 77 | 41 | 38 | 79 |
| 3 | " | 5.0 | $2.5 \times 10^{-4}$ | 91 | 46 | 40 | 86 |
| 4 | " | 6.0 | $2.4 \times 10^{-4}$ | 88 | 48 | 37 | 85 |
| 5 | " | 7.2 | $1.5 \times 10^{-4}$ | 85 | 55 | 32 | 87 |
| 6 | Manganese (II) acetate | 1.0 | $12.0 \times 10^{-4}$ | 70 | 32 | 18 | 50 |
| 7 | " | 2.0 | $9.7 \times 10^{-4}$ | 86 | 42 | 21 | 63 |
| 8 | " | 3.5 | $6.7 \times 10^{-4}$ | 93 | 50 | 36 | 86 |
| 9 | " | 6.5 | $5.7 \times 10^{-4}$ | 93 | 42 | 31 | 73 |

Reaction temperature:
Cobalt (II) acetate: 130° C.
Manganese (II) acetate: 160° C.
Concentration of catalyst: 0.2 mol/l
Precipitates of the catalyst were formed in Run Nos. 5 and 9.

Table IV

| Run No. | Catalyst | Reaction Temperature (°C.) | $k'_1$ (sec$^{-1}$) | Conversion (%) | $S_M$ (%) | $S_D$ (%) | $S_1$ (%) |
|---|---|---|---|---|---|---|---|
| 1 | Cobalt (II) acetate | 100 | $0.45 \times 10^{-4}$ | 60 | 43 | 20 | 63 |
| 2 | " | 120 | $1.39 \times 10^{-4}$ | 89 | 45 | 32 | 77 |
| 3 | " | 130 | $2.7 \times 10^{-4}$ | 91 | 47 | 38 | 85 |
| 4 | " | 140 | $4.1 \times 10^{-4}$ | 96 | 51 | 31 | 80 |
| 5 | " | 150 | $5.7 \times 10^{-4}$ | 90 | 43 | 33 | 76 |
| 6 | " | 180 | $17.3 \times 10^{-4}$ | 98 | 18 | 17 | 35 |
| 7 | manganese (II) acetate | 120 | $0.56 \times 10^{-4}$ | 68 | 39 | 14 | 53 |
| 8 | " | 140 | $1.9 \times 10^{-4}$ | 85 | 46 | 20 | 66 |
| 9 | " | 150 | $3.6 \times 10^{-4}$ | 92 | 49 | 27 | 76 |
| 10 | " | 160 | $6.6 \times 10^{-4}$ | 94 | 51 | 35 | 86 |
| 11 | " | 180 | $15.8 \times 10^{-4}$ | 98 | 33 | 29 | 62 |
| 12 | " | 200 | $45.0 \times 10^{-4}$ | 99 | 13 | 11 | 24 |

Concentration of catalyst: 0.2 mol/l
pH of aqueous liquid phase: 3.6 to 4.0

EXAMPLE 5

Using a 500 ml glass reactor equipped with the same devices as in Example 1, the same procedures as described in Run No. 2 in Example 1 were repeated. The results obtained are as follows:

| | |
|---|---|
| $k'_1$ | $4.6 \times 10^{-4}$ |
| Conversion | 93% |
| $S_M$ | 49% |
| $S_D$ | 36% |
| $S_1$ | 85% |

These values are almost the same as those obtained by using a titanium reactor.

EXAMPLE 6

Using a 500 ml SUS 32 (ASTM: A240 Type 316) reactor equipped with the same devices as in Example 1, the same procedures as described in Run No. 1 in Example 1 were repeated. The results obtained are shown in Table V.

Table V

| Run No. | $k'_1$ (sec$^{-1}$) | Conversion (%) | $S_M$ (%) | $S_D$ (%) | $S_1$ (%) |
|---|---|---|---|---|---|
| 1 | $4.5 \times 10^{-4}$ | 84 | 71 | 16 | 87 |
| 2 | $2.3 \times 10^{-4}$ | 75 | 75 | 8 | 83 |
| 3 | $0.7 \times 10^{-4}$ | 50 | 76 | 4 | 80 |

Note:
Run No. 1: A newly ground reactor was employed.
Run No. 2: A reactor covered with an oxidized surface in a passive state was employed.
Run No. 3: A reactor covered with a corroded surface after several uses was employed.

EXAMPLE 7

Using a 500 ml titanium reactor equipped with the same devices as in Example 1, the same procedures as described in Run No. 10 in Example 4 were repeated except that either the catalyst or the diethylbenzene recovered in Run No. 10 in Example 4 was employed. The results obtained are shown in Table VI below.

Table VI

| Run No. | $k'_1$ (sec$^{-1}$) | Conversion (%) | $S_M$ (%) | $S_D$ (%) | $S_1$ (%) |
|---|---|---|---|---|---|
| 1 | $6.4 \times 10^{-4}$ | 93 | 50 | 36 | 86 |
| 2 | $6.7 \times 10^{-4}$ | 96 | 48 | 34 | 82 |
| Example 4 Run No.3 | $6.6 \times 10^{-4}$ | 94 | 51 | 35 | 86 |

Note:
Run No. 1: Recovered diethylbenzene and newly prepared catalyst were employed.
Run No. 2: Recovered catalyst and newly prepared diethylbenzene were employed.

EXAMPLE 8

Into the same type of reactor as described in Example 1 were charged 240 g of ethylacetophenone and 60 g of a 0.2 mol/l aqueous cobalt acetate solution having a pH of 4.0 which had been prepared with acetic acid, and the oxidation reaction was carried out in the same manner as described in Example 1. The results obtained are shown in Table VII.

Table VII

| Run No. | $k'_2$ (sec$^{-1}$) | S* (%) | Conversion** (%) |
|---|---|---|---|
| 1 | $1.28 \times 10^{-4}$ | 88 | 60 |
| 2 | $1.29 \times 10^{-4}$ | 85 | 55 |

Note:
Run No. 1: The ethylacetophenone employed was that (para-isomer : meta-isomer weight ratio = 30 : 70)
Run No. 2: The ethylacetophenone employed was the p-ethylacetophenone obtained by acetylation of ethylbenzene.

$$*S = \frac{[DAB]}{[MAB]_o - [MAB]} \times 100$$

$$**\text{Conversion (\%)} = \frac{[MAB]_o - [MAB]}{[MAB]_o} \times 100$$

[DAB] and [MAB] each represents the molar concentration of diacetylbenzene and ethylacetophenone in the organic liquid phase after the oxidation reaction, respectively and [MAB]$_o$ represents the molar concentration of ethylacetophenone in the starting organic liquid phase.

EXAMPLE 9

Into a one liter titanium reactor equipped with two baffle plates, a stirrer, a gas inlet nozzle, a reflux condenser, a thermometer, a pressure gauge, a gas flow meter, a meter for measuring oxygen concentration, a nozzle for feeding the starting material and a nozzle for withdrawing the reaction mixture were charged 101 g of diethylbenzene (para-isomer:meta-isomer weight ratio=30:70), 177 g of ethylacetophenone (para-isomer:meta-isomer weight ratio=30:70) and 122 g of diacetylbenzene (para-isomer:meta-isomer weight ratio=30:70) and 140 g of a 0.2 mol/l aqueous cobalt (II) acetate solution having a pH of 4, and under stirring at a rate of 1,000 r.p.m. the temperature was increased to 140° C. under a nitrogen atmosphere and the pressure in the reactor was adjusted to 15 Kg/cm². Under these conditions air as the molecular oxygen-containing gas was fed thereto at a rate of 60 l/minute (N.T.P.), and after the absorption of oxygen started diethylbenzene (para-isomer:meta-isomer weight ratio=30:70) at a rate of 1.61 moles/hour, ethylacetophenone (para-isomer:meta-isomer weight ratio=30:70) at a rate of 1.24 moles/hour and a 0.2 mol/l aqueous cobalt (II) acetate solution at a rate of 100 g/hour were continuously fed into the reactor. During the reaction the reaction mixture liquid was withdrawn while maintaining the level of the reaction mixture liquid in the reactor constant. The oxidation reaction achieved a stationary state in 3 to 8 hours from the start of the oxidation reaction, and in this period diethylbenzene at a rate of 0.58 mole/hour, ethylacetophenone at a rate of 1.28 moles/hour, diacetylbenzene at a rate of 0.81 mole/hour and the aqueous liquid phase at a rate of 140 g/hour were withdrawn. At this time the selectivity $S_2$ was 79% and the recovery rate of cobalt (II) acetate was 98%.

EXAMPLE 10

Into the same type of reactor as described in Example 9 were charged 95.6 g of diethylbenzene (para-isomer:meta-isomer weight ratio=30:70), 218 g of ethylacetophenone (para-isomer:meta-isomer weight ratio=30:70), 86.4 g of diacetylbenzene (para-isomer:meta-isomer weight ratio=30:70) and 130 g of a 0.2 mol/l aqueous cobalt (II) acetate solution having a pH of 4, and under stirring at a rate of 1,000 r.p.m. the temperature was increased to 125° C. under a nitrogen atmosphere and the pressure in the reactor was adjusted to 15 Kg/cm². Under these conditions air as the molecular oxygen-containing gas was fed thereto at a rate of 60 l/minute (N.T.P.), and after the absorption of oxygen started diethylbenzene (para-isomer:meta-isomer weight ratio=30:70) at a rate of 1.32 moles/hour, ethylacetophenone (para-isomer:meta-isomer weight ratio=30:70) at a rate of 1.51 moles/hour and a 0.2 mol/l aqueous cobalt (II) acetate solution at a rate of 100 g/hour were continuously fed into the reactor. During the reaction mixture liquid was withdrawn while maintaining the level of the reaction mixture liquid in the reactor constant. In the period 3 to 8 hours after the start of the oxidation reaction, diethylbenzene at a rate of 0.71 mole/hour, ethylacetophenone at a rate of 1.49 moles/hour, diacetylbenzene at a rate of 0.54 and the aqueous liquid phase at a rate of 130 g/hour were withdrawn. At this time the selectivity $S_2$ was 88% and the recovery rate of cobalt (II) acetate was 98%.

EXAMPLE 11

Into a 1,000 ml titanium reactor equipped with the same devices as the reactor of Example 1 were charged 480 g of diethylbenzene (para-isomer:meta-isomer weight ratio=30:70) and 120 g of a 0.2 mol/l aqueous cobalt (II) acetate solution having a pH of 4, and the oxidation reaction was carried out at 130° C. with stirring at a rate of 1,000 r.p.m. in the same manner as described in Example 1.

240 Minutes after the start of the oxidation reaction the conversion of diethylbenzene became 87%, and the amount of the components of the organic liquid phase at this time determined by gas chromatography are shown in Table VIII below. Also at this time the reaction mixture liquid was withdrawn and separated into the organic liquid phase and the aqueous liquid phase by passing the reaction mixture liquid through a glass column of 50 mm in diameter and 20 cm in length packed with glass wool and allowing the reaction mixture liquid passed to settle. Then, the organic liquid phase separated in this manner was distilled to obtain each component of the product. The results are also shown in Table VIII. The amount of cobalt in the aqueous liquid phase obtained by chelatometric titration was 0.98 mole which corresponded to 98% of the amount of cobalt fed.

Table VIII

| Component | Amount of Feed (g) | Amount of Product (g) | Amount of Product after Distillation (g) | Recovery Rate by Distillation (%) |
| --- | --- | --- | --- | --- |
| DEB | 480 | 61 | 61 | 100 |
| MAB | 0 | 220 | 217 | 98.6 |
| DAB | 0 | 201 | 195 | 97.0 |
| Alcohols* | 0 | 47 | 45 | 95.7 |
| Others | 0 | 11** | 16*** | — |
| Total | 480 | 540 | 534 | — |

Note:
DEB: Diethylbenzene
MAB: Ethylacetophenone
DAB: Diacetylbenzene
*Alcohols corresponding to MAB and DAB.
**Weight = Total weight - (DEB + MAB + DAB + Alcohols) weight
***Distillation residue

EXAMPLE 12

The same procedures as described in Example 11 were repeated. The conversion of diethylbenzene was 88% and a reaction mixture liquid containing an organic liquid phase of 11 percent by weight of diethylbenzene, 41 percent by weight of ethylacetophenone, 38 percent by weight of diacetylbenzene, 7 percent by weight of alcohols and 3 percent by weight of other materials was obtained. Then, the organic liquid phase was separated from the aqueous liquid phase and divided into three parts. After each part had been treated with an aqueous solution as set forth in Table IX below, the resultant solution was distilled. The results obtained are shown in Table IX.

Table IX

| Run No. | Aqueous solution (ml) | Recovery Rate of DAB (%) | Amount of Distillation Residue (% by weight based on total feed in distillation) |
| --- | --- | --- | --- |
| 1 | 0.1 N Aqueous hydrochloric acid solution (200) | 98 | 2.5 |
| 2 | 0.1 N Aqueous sodium hydroxide solution (200) | 98 | 2.0 |
| 3 | 0.1 N Aqueous sodium hydroxide solution (200) first and then 0.1 N aqueous hydrochloric acid solution (200) | 98.5 | 1.0 |

DAB : Diacetylbenzene

While the invention has been described in detail and with reference to specific embodiments thereof, it will be apparent to one skilled in the art that various changes and modifications can be made therein without departing from the spirit and scope thereof.

What is claimed is:

1. A process for preparing diacetylbenzene using a liquid phase oxidation reaction which comprises contacting a heterogenous mixture of (A) about 98 to about 25 percent by volume of an organic liquid phase containing at least one compound selected from the group consisting of diethylbenzene and ethylacetophenone and (B) about 2 to about 75 percent by volume of an aqueous liquid phase containing, as a catalyst, at least about 0.01 mol/l of at least one water-soluble salt selected from the group consisting of the acetates, propionates, sulfates, nitrates and chlorides of manganese (II), cobalt (II), nickel (II), chromium (III), copper (II) and iron (III) and having a pH of about 1 to about 6 with a molecular oxygen-containing gas at a temperature of about 100° C. to about 180° C. under a pressure of about 1 to about 50 Kg/cm² to effect liquid phase oxidation reaction; separating the resulting reaction mixture into the aqueous liquid phase and the organic liquid phase; and recovering diacetylbenzene from the separated organic liquid phase by distillation.

2. The process as claimed in claim 1, wherein the watersoluble salt of a metal is cobalt (II) acetate.

3. The process as claimed in claim 2, wherein the oxidation reaction temperature ranges from 120° C. to 150° C.

4. The process as claimed in claim 1, wherein the watersoluble salt of a metal is manganese (II) acetate.

5. The process as claimed in claim 4, wherein the oxidation reaction temperature ranges from 130° C. to 160° C.

6. The process as claimed in claim 1, wherein the concentration of the catalyst in the aqueous liquid phase ranges from 0.1 to 1.0 mol/l.

7. The process as claimed in claim 1, wherein the pH of the aqueous liquid phase ranges from 3 to 5.

8. The process as claimed in claim 1, wherein the amount of the aqueous liquid phase based on the total amount of the organic liquid phase and the aqueous liquid phase ranges from 10 to 50 percent by volume.

9. The process as claimed in claim 1, wherein the molecular oxygen-containing gas is air.

10. The process as claimed in claim 1, wherein the amount of the molecular oxygen based on the total gas in a reactor ranges from 2 to 10 percent by volume.

11. The process as claimed in claim 1, wherein the contacting is in a titanium reactor or a titanium-lined reactor.

12. The process as claimed in claim 1, wherein the contacting is in a glass reactor or a glass-lined reactor.

13. The process as claimed in claim 1, wherein the contacting is in a reactor whose parts in contact with the reaction mixture liquid are lined with titanium.

14. The process as claimed in claim 1, wherein the contacting is in a reactor whose parts in contact with the reaction mixture liquid are lined with glass.

15. The process as claimed in claim 1, which includes recovering at least one compound selected from the group consisting of diethylbenzene and ethylacetophenone by distillation from the organic liquid phase after the liquid phase oxidation reaction and reusing the compound recovered as a starting material for the liquid phase oxidation reaction.

16. The process as claimed in claim 1, which includes treating the organic liquid phase separated from the aqueous liquid phase after the liquid phase oxidation reaction with at least one aqueous solution selected from the group consisting of an aqueous acidic solution and an aqueous alkaline solution, again separating the organic liquid phase formed and recovering diacetylbenzene from the resulting organic liquid phase by distillation.

17. The process as claimed in claim 1, which comprises adjusting the concentration and pH of the aqueous liquid phase separated from the organic liquid phase after the liquid phase oxidation reaction to at least about 0.01 mol/l and about 1 to about 6, respectively, and reusing the resulting aqueous liquid phase for the liquid phase oxidation reaction.

* * * * *